United States Patent
Badawy et al.

(10) Patent No.: US 11,896,586 B2
(45) Date of Patent: Feb. 13, 2024

(54) APIXABAN FORMULATIONS

(71) Applicants: Bristol-Myers Squibb Company, Princeton, NJ (US); Pfizer Inc., New York, NY (US)

(72) Inventors: Sherif Ibrahim Farag Badawy, Dayton, NJ (US); Timothy D. Stevens, Skillman, NJ (US); Daniel Kuntz, Bend, OR (US); Brett Waybrant, Bend, OR (US)

(73) Assignees: Bristol-Myers Squibb Company, Princeton, NJ (US); Pfizer Inc., New York, NY (US)

( * ) Notice: Subject to any disclaimer, the term of this patent is extended or adjusted under 35 U.S.C. 154(b) by 587 days.

(21) Appl. No.: 17/047,428

(22) PCT Filed: Apr. 15, 2019

(86) PCT No.: PCT/US2019/027456
§ 371 (c)(1),
(2) Date: Oct. 14, 2020

(87) PCT Pub. No.: WO2019/204193
PCT Pub. Date: Oct. 24, 2019

(65) Prior Publication Data
US 2021/0145817 A1 May 20, 2021

Related U.S. Application Data (60) Provisional application No. 62/658,175, filed on Apr. 16, 2018.

(51) Int. Cl.
| | | |
|---|---|---|
| A61K 31/4545 | (2006.01) | |
| A61K 9/00 | (2006.01) | |
| A61K 9/16 | (2006.01) | |
| A61K 9/48 | (2006.01) | |

(52) U.S. Cl.
CPC ........ *A61K 31/4545* (2013.01); *A61K 9/0095* (2013.01); *A61K 9/1623* (2013.01); *A61K 9/1652* (2013.01); *A61K 9/1676* (2013.01); *A61K 9/4808* (2013.01); *A61K 9/4816* (2013.01); *A61K 9/4825* (2013.01)

(58) Field of Classification Search
CPC .............. A61K 31/4545; A61K 9/0095; A61K 9/1623; A61K 9/1652; A61K 9/1676; A61K 9/4808; A61K 9/4816; A61K 9/4825; A61P 7/02
See application file for complete search history.

(56) References Cited

U.S. PATENT DOCUMENTS

| | | |
|---|---|---|
| 6,967,208 B2 | 11/2005 | Pinto et al. |
| 9,326,945 B2 | 5/2016 | Patel et al. |
| 2012/0087978 A1 | 4/2012 | Nause |
| 2013/0045245 A1 | 2/2013 | Patel et al. |
| 2016/0263097 A1* | 9/2016 | Badawy ................. A61K 47/32 |
| 2017/0056401 A1* | 3/2017 | Dharmadikari ...... A61K 9/5042 |

FOREIGN PATENT DOCUMENTS

| | | | | |
|---|---|---|---|---|
| CN | 105663049 A | | 6/2016 | |
| CN | 106913528 A | * | 7/2017 | ......... A61K 31/4545 |
| CN | 106913528 A | | 7/2017 | |
| EP | 0559463 A1 | * | 8/1993 | ............... A61K 9/16 |
| EP | 2554159 A1 | * | 2/2013 | ......... A61K 31/4545 |
| JP | 2012-530141 A | | 11/2012 | |
| WO | WO-9842318 A1 | * | 10/1998 | ........... A61K 31/496 |
| WO | 2014/027334 A2 | | 2/2014 | |

OTHER PUBLICATIONS

Communication Pursuant to Article 94(3) EPC in European Application No. 19722333.2 (dated Aug. 2022).
Office Action in Mexican Application No. MX/a/2020/010673 (dated Sep. 2022).
Second Office Action in Mexican Application No. MX/a/2020/010673 (Feb. 2023).
Yoichi Ishikawa et al., "Issues and Solutions for Early Commercialization of Pediatric Formulations: Contributing to Early Commercialization of Pediatric Drugs. Regulatory Science Research Group Report," 76(5) Pharmaceutics 324-339 (2016).
Notice of Reasons for Refusal in Japanese Application No. 2020-556976 (dated Mar. 2023).
Notice of Reasons for Refusal in Japanese Application No. 2020-556976 (dated Jul. 2023).

\* cited by examiner

*Primary Examiner* — Aradhana Sasan
(74) *Attorney, Agent, or Firm* — Venable LLP

(57) ABSTRACT

Apixaban pharmaceutical formulation is provided. Also provided is a use of the apixaban formulation in treatment of a thromboembolic disorder.

45 Claims, 3 Drawing Sheets

FIG. 1

Forest Plot of Adjusted GMR of Cmax and AUC for Apixaban 25 × 0.1-mg Sprinkle Capsules vs Apixaban 5 × 0.5-mg Tablets (Evaluable Pharmacokinetic Population)

GMR = geometric mean ratio

Treatments: A = 5 × 0.5-mg apixaban tablets; B = 25 × 0.1-mg apixaban sprinkle capsules The filled circle and line represent the point estimate and 90% confidence interval of the geometric mean ratio relative to the reference treatment.

Dashed lines are drawn at 0.8, 1.00, and 1.25.

FIG. 2

Mean (+SD) Apixaban Plasma Concentration Profile vs Time
(Evaluable Pharmacokinetic Population)

h = hour; LLOQ = lower limit of quantification; SD = standard deviation
Treatments: A = 5 × 0.5-mg apixaban tablets; B = 25 × 0.1-mg apixaban sprinkle capsules
Dotted line represents LLOQ (1.00 ng/mL). Less than LLOQ values were treated as "missing" for calculation of mean and SD values.

FIG. 3

APIXABAN FORMULATIONS

CROSS-REFERENCE TO RELATED APPLICATIONS

This application claims the benefit of Provisional Application No. 62/658,175, filed Apr. 16, 2018, which is incorporated herein by reference in its entirety.

FIELD OF THE INVENTION

This invention relates to apixaban pharmaceutical formulations.

BACKGROUND OF THE INVENTION

Apixaban is a known compound having the structure:

The chemical name for apixaban is 4,5,6,7-tethydro-1-(4-methoxyphenyl)-7-oxo-6-[4-(2-oxo-1-piperidinyl)phenyl]-1H-pyrazolo[3,4-c]pyridine-3-carboxamide (CAS name) or 1-(4-methoxyphenyl)-7-oxo-6-[4-(2-oxo-1-piperidinyl)phenyl]-4,5,6,7-tetrahydro-1H-pyrazolo[3,4-c]pyridine-3-carboxamide (IUPAC name).

Apixaban is disclosed in U.S. Pat. No. 6,967,208 and in U.S. Patent Application Publication Nos. 2012/0087978 and 2013/0045245, which are all herein incorporated by reference in their entirety. Apixaban has utility as a Factor Xa inhibitor, and is being developed for oral administration in a variety of indications that require the use of an antithrombotic agent, such as in patients following elective hip or knee surgery and stroke prevention in atrial fibrillation or for treatment of venous thrombosis.

There is an on-going need for formulations for administration of apixaban to the pediatric population and to adults who are unable to swallow a solid dosage form.

SUMMARY OF THE INVENTION

Disclosed herein is a formulation comprising apixaban.

In an embodiment of the present invention, the formulation is suitable for dispersion and/or dissolution in food or beverages. In an embodiment, the formulation is contained in a sprinkle capsule (i.e., a capsule for sprinkle, dispersion and/or dissolution).

In an embodiment, the formulation comprises at least one treated core. In an embodiment, the formulation comprises numerous treated cores. In an embodiment, the treated core can comprise a core substrate, such as a sugar sphere or bead, or a microcrystalline cellulose, lactose, and/or mannitol particle, to which apixaban is applied. The treated core or cores may be placed in a capsule.

Another embodiment of the present invention is a method for treating a thromboembolic disorder, comprising administering to a patient in need thereof a therapeutically effective amount of the formulation comprising apixaban.

DETAILED DESCRIPTION OF THE INVENTION

Oral administration of solid dosage forms of apixaban (such as tablets or capsules) to patients who have difficulty swallowing is challenging. Studies were conducted to develop a solid formulation of apixaban that is suitable for dispersion and/or dissolution, for instance, in food or beverages, in order to facilitate oral administration.

Because of the low body mass of neonates, infants, and even children, a small dose of apixaban may be needed, for example, as little as 0.1 mg of apixaban. Moreover, because the body mass of neonates, infants, and children increases proportionally rapidly with age, it is important to be able to administer varying doses of apixaban with a narrow increment (e.g., 0.1 mg, 0.2 mg, 0.3 mg, 0.4 mg). At such low doses, it is challenging to make a dosage form that provides adequate uniformity of dosing of apixaban. Traditionally, volumetrically dispensed liquid formulations have been used for low incremental dosing of pharmaceuticals. However, it has now been found that good content uniformity of solid apixaban dosage forms, particularly at low doses mentioned above, can be achieved using treated cores as described herein.

In an embodiment, the formulation comprises at least one treated core. In an embodiment, the formulation comprises numerous treated cores. In an embodiment, the treated core comprises a core substrate. This core substrate, for instance, may be of various shapes and sizes, and may be a bead or a sphere. The core substrate may be solid or hollow. In an embodiment, the core substrate is a sugar particle, such as a sugar bead or sphere. In an embodiment, the sugar bead or sphere comprises at least one of sugar syrup, corn starch, and sucrose. Suitable sugar spheres include SUGLETS® that can be purchased from Colorcon, Harleysville, PA In an embodiment, the core substrate is a microcrystalline cellulose, lactose, and/or mannitol particle. In an embodiment, the core substrate comprises at least about 75% w/w, at least about 80% w/w, at least about 85% w/w, at least about 90% w/w, or at least about 95% w/w of the formulation. In an embodiment, the core substrate comprises from about 89% w/w to about 91% w/w of the formulation. In another embodiment, the core substrate is a sugar sphere or bead, which comprises about 90% w/w of the formulation. The size of the core substrate may be, for example, from about 180 microns to about 250 microns.

In an embodiment, the treated core further comprises a carrier that facilitates attachment or adhesion of apixaban to the treated core before dispersion and/or dissolution in food or beverage. The carrier may comprise one or more compounds. Suitable carriers include binders and/or film forming agents. Suitable binders and film forming agents are listed, for example, in the Handbook of Pharmaceutical Excipients, 8<sup>th</sup> Ed. The carrier preferably has good water solubility. Suitable examples include a cellulosic compound. In an embodiment, the carrier is hydroxypropylcellulose (HPC) and/or hypromellose (HPMC). Suitable hydroxypropylcelluose includes Klucel™-EF that can be purchased from Ashland, Covington, KY, and Nisso HPC-LM that can be purchased from Nisso America, New York, NY Suitable hypromellose includes Methocel™ E5 Premium LV HPMC that can be purchased from Dow Chemical Company, Midland, MI In an embodiment, the treated core and/or the formulation that contains at least one treated core may include at least about 1% w/w carrier, at least about 5% w/w carrier, at least about 9% w/w carrier, at least about 10% w/w carrier, at least about 11% w/w carrier, or any amount there between. In an embodiment, the treated core and/or the formulation that contains at least one treated core comprises from about 9% w/w carrier to about 11% w/w carrier. In an embodiment, the treated core and/or the formulation that contains at least one treated core comprises from about 9.6% w/w carrier to about 10.2% w/w carrier. In another embodiment, the treated core and/or formulation that contains at least one treated core comprises about 9.9% w/w carrier. The carrier may, for example, form a continuous film that incorporates apixaban over the core substrate, or it may improve the ability of apixaban to stick to the surface of the core substrate.

The size of the treated core may be up to about 150 microns, at least about 150 microns, at least about 180 microns, at least about 200 microns, at least about 212 microns, at least about 250 microns, at least about 300 microns, at least about 355 microns, or any size therebetween. The size of the treated core, for example, may be up to about 355 microns. In an embodiment, the size of the treated core is from about 150 microns to about 355 microns. In an embodiment, the size of the treated core is from about 150 microns to about 300 microns. In an embodiment, the size of the treated core is from about 180 microns to about 250 microns. In an embodiment, the size of the treated core is from about 212 microns to about 250 microns. In an embodiment, the size of the treated core is from about 250 microns to about 300 microns.

Figure 3:
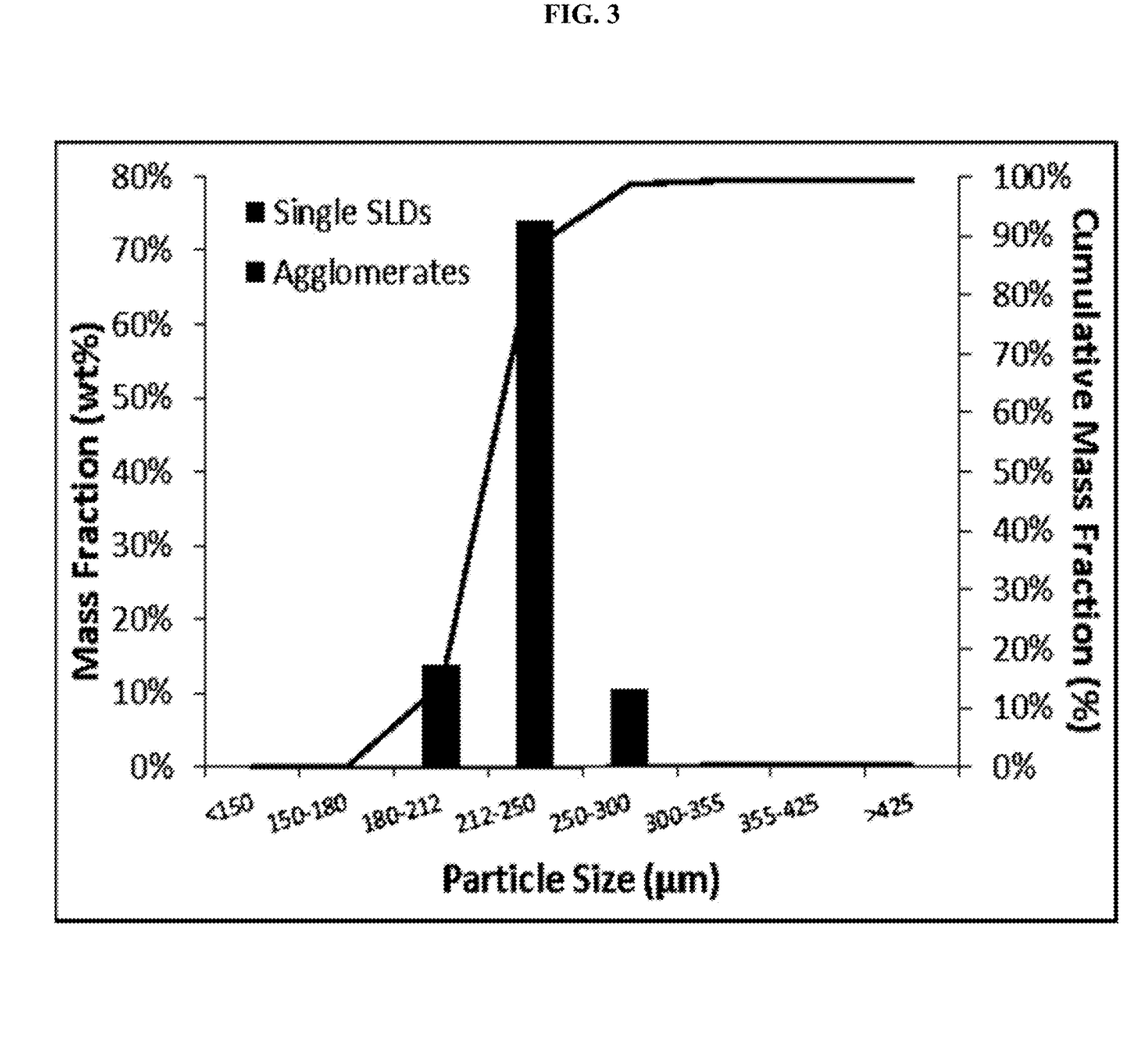
FIG. 3 shows a size distribution of the treated cores.

In an embodiment, the sizes of the of the treated cores exhibit a size distribution. In an embodiment, the treated cores comprise at least about 60% w/w treated cores of size about 212 to about 250 microns, at least about 70% w/w treated cores of size about 212 to about 250 microns, at least about 80% w/w treated cores of size about 212 to about 250 microns or any amount therebetween. In an embodiment, the treated cores comprise from about 60% w/w to about 80% w/w treated cores of size from about 212 to about 250 microns. In an embodiment, the treated cores comprise from about 70% w/w to about 80% w/w treated cores of size from about 212 to about 250 microns. In an embodiment, the treated cores comprise from about 5.0% w/w to about 15% w/w treated cores of size from about 180 to about 212 microns, from about 60% w/w to about 80% w/w treated cores of size from about 212 to about 250 microns, and from about 5.0% w/w to about 15% w/w treated cores of size from about 250 to about 300 microns. In an embodiment, the treated cores comprise about 13% w/w treated cores of size from about 180 to about 212 microns, about 74% w/w treated cores of size from about 212 to about 250 microns, and about 10% w/w treated cores of size from about 250 to about 300 microns. A size distribution of the treated cores is shown in FIG. 3. Treated core size and treated core size distribution may be determined by sieve analysis (i.e., by passage through sieves of progressively smaller mesh size).

It is thought that the selection of an appropriate treated core size distribution contributes to content uniformity of apixaban in the formulation. A narrow treated core size distribution can be beneficial in providing good content uniformity. In an embodiment, from about 60% w/w to about 90% w/w of the treated cores are within from about 1% to about 20% of the mean treated core size. In an embodiment, from about 60% w/w to about 90% w/w of the treated cores are within from about 5% to about 15% of the mean treated core size. In an embodiment, from about 70% w/w to about 80% w/w of the treated cores are within from about 1% to about 20% of the mean treated core size. In an embodiment, from about 70% w/w to about 80% w/w of the treated cores are within from about 5% to about 15% of the mean treated core size. In an embodiment, about 74% w/w of the treated cores are within about 12% of the mean treated core size. Desirable treated core size distribution may be exercised by controlling or selecting the size of the core substrates used to form the treated core and/or the application of the carrier and apixaban thereon, for instance, via the technique of spray-layered dispersion (SLD). For example, core substrates may be selected so as to have the above-mentioned deviation from the mean core substrate size.

Agglomerates of the treated cores may be present. These agglomerates may be twins and/or triplets. In an embodiment, the treated cores may be passed through a sieve to remove agglomerates, for example, a 300 micron sieve.

Apixaban in the treated core and/or in the formulation that contains at least one treated core may be in crystalline and/or amorphous form. For instance, it may be Form N-1 (neat) and/or Form H2-2 (hydrate) of apixaban.

Form N-1 (neat) and Form H2-2 (hydrate) of apixaban may be characterized by unit cell parameters substantially equal to the following shown in Table 1.

TABLE 1

| Form | N-1 | H2-2 |
|---|---|---|
| Solvate | None | Dihydrate |
| T | +22 | +22 |
| a (Å) | 10.233 | 6.193 |
|  | (1) | (1) |
| b (Å) | 13.852 | 30.523 |
|  | (1) | (1) |
| c (Å) | 15.806 | 13.046 |
|  | (1) | (1) |
| α, ° | 90 | 90 |
| β, ° | 92.98 | 90.95 |
|  | (1) | (1) |
| γ, ° | 90 | 90 |
| V (Å$^3$) | 2237.4 | 2466.0 |
|  | (5) | (5) |
| Z' | 1 | 1 |
| Vm | 559 | 617 |
| SG | P2$_1$/n | P2$_1$/n |
| Dcalc | 1.364 | 1.335 |
| R | 0.05 | 0.09 |
| Sol. sites | None | 2 H$_2$O |

Z' is the number of molecules per asymmetric unit.
T(° C.) is the temperature for the crystallographic data.
Vm=V(unit cell)/(ZZ')

Characteristic X-ray diffraction peak positions (degrees 2θ±0.1) at room temperature, based on a high quality pattern collected with a diffractometer (CuKα) with a spinning capillary with 2θ calibrated with a NIST suitable standard are shown in Table 2 below.

TABLE 2

| Form N-1 | Form H2-2 |
|---|---|
| 10.0 | 5.8 |
| 10.6 | 7.4 |
| 12.3 | 16.0 |
| 12.9 | 20.2 |
| 18.5 | 23.5 |
| 27.1 | 25.1 |

The treated core and/or the formulation that contains at least one treated core may include at least about 0.001% w/w apixaban, at least about 0.01% w/w apixaban, at least about 0.05% w/w apixaban, at least about 0.07% w/w apixaban, at least about 0.09% w/w apixaban, at least about 0.1% w/w apixaban, at least about 0.11% w/w apixaban, at least about 0.12% w/w apixaban, at least about 0.13% w/w apixaban, at least about 0.14% w/w apixaban, at least about 0.15% w/w apixaban, at least about 0.20% w/w apixaban, or any amount therebetween. In an embodiment, the treated core and/or the formulation that contains at least one treated core comprises from about 0.001% w/w to about 0.20% w/w apixaban. In another embodiment, the treated core and/or the formulation that contains at least one treated core comprises from about 0.01% w/w to about 0.15% w/w apixaban. In another embodiment, the treated core and/or the formulation that contains at least one treated core comprises from about 0.09% w/w to about 0.11% w/w apixaban. In another embodiment, the treated core and/or the formulation that contains at least one treated core comprises about 0.1% w/w apixaban.

In an embodiment, the mass ratio of apixaban to carrier is at least about 90:10, at least about 95:5, at least about 99:1, at least about 99.5:0.5, or any amount therebetween. In an embodiment the ratio of apixaban to carrier is from about 95:5 to about 99.5:0.5. In an embodiment the ratio of apixaban to carrier is about 99:1.

In an embodiment, the formulation further comprises an anti-adherent. In an embodiment, the anti-adherent is talc, starch, microcrystalline cellulose (MCC) and/or HPMC. The anti-adherent may reduce or eliminate clumping of the treated cores. Suitable starch includes starch 1500 that can be purchased from Colorcon Inc., Harleysville, PA Suitable microcrystalline cellulose includes Avicel® PH105 that can be purchased from DuPont Co., Wilmington, DE Suitable HPMC includes Methocel-m E5 Premium LV HPMC that can be purchased from Dow Chemical Company, Midland, MI.

In an embodiment, the formulation may include at least about 1% w/w anti-adherent, at least about 2% w/w anti-adherent, at least about 3% w/w anti-adherent, at least about 4% w/w anti-adherent, at least about 5% w/w anti-adherent, or any amount there between. In an embodiment, the formulation comprises from about 1% w/w anti-adherent to about 5% w/w anti-adherent. In an embodiment, the formulation comprises from about 2% w/w anti-adherent to about 3% w/w anti-adherent. In an embodiment, the formulation comprises about 2% w/w anti-adherent. In another embodiment, the formulation comprises about 3% w/w anti-adherent. If an anti-adherent is used, it is dry-blended with the treated cores of the formulation.

In an embodiment, the treated core and/or the formulation that contains at least one treated core has a water content. In an embodiment, the water content may be at least about 0.5% w/w, at least about 1.0% w/w, at least about 1.5% w/w, at least about 2.0% w/w, or any amount therebetween. In an embodiment, the water content of the treated core and/or the formulation that contains at least one treated core is from about 0.5% w/w to about 2.0% w/w. In another embodiment, the water content of the treated core and/or the formulation that contains at least one treated core is from about 1.0% w/w to about 1.5% w/w. In an embodiment, the water content is about 1.3% w/w. The water content may be determined by Karl Fisher titration using a coulometric oven method.

In an embodiment, the treated core and/or the formulation comprises less than about 300 ppm of ethanol, less than about 200 ppm of ethanol, less than about 100 ppm of ethanol, less than about 50 ppm of ethanol, less than about 25 ppm of ethanol or any amount therebetween. In an embodiment, the treated core and/or the formulation comprises from about 25 ppm to about 300 ppm of ethanol. In an embodiment, the treated core and/or the formulation comprises from about 25 ppm to about 100 ppm of ethanol.

In an embodiment, the formulation is a capsule that contains at least one treated core. The capsule may be openable to release its contents into a vehicle for administration, such as a liquid medium or a non-liquid food item in which it can be mixed, dispersed and/or dissolved. In another embodiment, at least one treated core is contained in a stickpack or pouch.

In an embodiment, the mass of the contents of the capsule may be at least about 85 mg, at least about 100 mg, at least about 115 mg, or any amount therebetween. In an embodiment, the mass of the contents of the capsule is from about 85 mg to about 115 mg. In an embodiment, the mass of the contents of the capsule is about 100 mg. The stickpack or pouch may be filled in the same manner. Optionally, the capsule, stickpack and/or pouch or the like may include contents other than the treated cores. Such contents may include, for example, at least one an anti-adherent, filler, flavorant, or another inactive ingredient suitable for administration to the subject being treated.

In an embodiment, the mass of the filled capsule may be at least about 180 mg, at least about 195 mg, at least about 215 mg, or any amount therebetween. In an embodiment, the mass of the filled capsule is from about 180 mg to about 215 mg. In an embodiment, the mass of the filled capsule is about 194 mg. In an embodiment, the mass of the filled capsule is about 196 mg.

In an embodiment, the capsule is filled to at least about 5% of its fill capacity, at least about 10a of its fill capacity, at least about at least about 15% of its fill capacity, at least about 20% of its fill capacity, at least about 25% of its fill capacity, at least about 50% of its fill capacity or any amount therebetween.

In an embodiment, the capsule is filled from about 5% to about 50% of its fill capacity. In an embodiment, the capsule is filled from about 10% to about 25% of its fill capacity. In an embodiment, the capsule is filled from about 15% to about 20% of its fill capacity.

The capsule may be a so-called sprinkle capsule. Sprinkle capsules are designed to be easily opened by patients or caregivers so that the formulation can be dispersed and/or dissolved in food or beverages, such as formula or water. In an embodiment, the formulation is dispersed and/or dissolved in at least about 1 mL of beverage, at least about 2.5 mL of beverage, at least about 4.0 mL of beverage, at least about 5.0 mL of beverage, at least about 6.0 mL of beverage, at least about 10 mL of beverage, at least about 50 mL of beverage, at least about 100 mL of beverage, at least about 250 mL of beverage or any amount therebetween. In an embodiment, the formulation is dispersed and/or dissolved in from about 1 mL to about 250 mL of beverage. In an embodiment, the formulation is dispersed and/or dissolved in from about 1 mL to about 50 mL of beverage. In an embodiment, the formulation is dispersed and/or dissolved in from about 1 mL to about 10 mL of beverage. In an embodiment, the formulation is dispersed and/or dissolved in from about 2.5 mL to about 5 mL of beverage. In an embodiment, the formulation is dispersed and/or dissolved in about 2.5 mL of beverage. In an embodiment, the formulation is dispersed and/or dissolved in from about 4 mL to about 6 mL of beverage. In an embodiment, the formulation is dispersed and/or dissolved in about 5 mL of beverage. In the case of a neonate or infant subject, the volume of beverage that can be safely administered is limited by the small body mass.

The sprinkle capsule enables consistent dosing of the formulation, which is advantageous for consistent low-dosing of apixaban. Suitable sprinkle capsules include Coni-Snap® Sprinkle capsules that can be purchased from Capsugel, Morristown, NJ In an embodiment the sprinkle capsule has a transparent end and an opaque end that may be colored.

In an embodiment, the capsule is a gelatin capsule or an HPMC capsule.

In an embodiment, the treated core and/or the formulation that contains at least one treated core is encapsulated manually or with a suitable encapsulator such as the IMA Zanasi Plus 70 E capsule filler that can be purchased from Industria Macchine Automatiche S.P.A., Italy.

In an embodiment, the capsule may comprise at least about 0.05 mg of apixaban, at least about 0.1 mg of apixaban, at least about 0.25 mg of apixaban, at least about 0.3 mg of apixaban, at least about 0.5 mg of apixaban, at least about 1.0 mg of apixaban, at least about 2.5 mg of apixaban, at least about 5.0 mg of apixaban, or any amount therebetween. In an embodiment the capsule comprises between about 0.05 mg of apixaban and 5.0 mg of apixaban. In an embodiment the capsule comprises between about 0.05 mg of apixaban and about 0.3 mg of apixaban. In an embodiment, the capsule comprises about 0.1 mg of apixaban. In an embodiment, the capsule comprises about 0.25 mg of apixaban.

In an embodiment, the treated core is made by applying a solution or dispersion comprising apixaban and carrier in a solvent onto a core substrate, such as a sugar sphere or bead. Preferably, the solution or dispersion is sprayed onto the core substrate, for example, by the technique of spray-layered dispersion (SLD). This may be accomplished in a spray or fluid bed coater such as a Niro MP-1 or MP-2 fluid bed that can be purchased from GEA Group AG, Dusseldorf, Germany. A Wurster-style plate may be used in the coating process. Suitable solvents include water, acetone, an alcohol (such as methanol, ethanol and/or isopropanol), and mixtures thereof. The solvent may be, for example, a mixture of ethanol and water (such as about 90:10 ethanol:water) or a mixture of methanol and ethanol (such as about 90:10 ethanol:methanol). In an embodiment, the solubility of apixaban in the solvent may be at least about 0.02% w/w, at least about 0.05% w/w, at least about 0.10% w/w, at least about 0.20% w/w, or any concentration therebetween. In an embodiment, the solubility of apixaban in the solvent is from about 0.02% w/w to about 0.20% w/w. In an embodiment, the solubility of apixaban in the solvent is from about 0.05% w/w to about 0.10% w/w. In an embodiment, the solubility of apixaban in the solvent is about 0.06% w/w. Preferably, the SLD process is carried out with a concentration of apixaban in the solvent below the solubility limit, for example, below about 60% of the solubility limit, below about 40% of the solubility limit, below about 20% of the solubility limit, or any concentration therebetween. In an embodiment, the concentration of apixaban in the solvent is from about 20% to about 60% of the solubility limit. In an embodiment, the concentration of apixaban in the solvent is about 40% of the solubility limit. In an embodiment, the concentration of apixaban in the solvent may be at least about 0.01% w/w, at least about 0.02% w/w, at least about 0.03% w/w, at least about 0.04% w/w, or any concentration therebetween. In an embodiment, the concentration of apixaban in the solvent is from about 0.01% w/w to about 0.04% w/w. In an embodiment, the concentration of apixaban in the solvent is from about 0.02% w/w to about 0.03% w/w. In an embodiment, the concentration of apixaban in the solvent is about 0.022% w/w. In an embodiment, the concentration of total solids dissolved in the solvent may be at least about 1.0% w/w, at least about 2.0% w/w, at least about 3.0% w/w, or any concentration therebetween. In an embodiment, the concentration of total solids in the solvent is from about 1.0% w/w to about 3.0% w/w. In an embodiment, the concentration of total solids in the solvent is about 2.0% w/w.

Residual solvent may be removed in one or more subsequent drying steps. For example, by in situ fluid bed drying or tray drying. As a result, a layer, such as a film or coating, containing the carrier and apixaban, may be formed on the core substrate. In an embodiment, the thickness of the layer is at least about 1 micron, at least about 2.5 microns, at least about 5 microns, at least about 7.5 microns, at least about 10 microns, at least about 25 microns or any amount therebetween. In an embodiment, the thickness of the layer is from about 1 micron to about 25 microns. In an embodiment, the thickness of the layer is from about 5 microns to about 10 microns. In an embodiment, the thickness of the layer is from about 4 microns to about 6 microns. In an embodiment, the thickness of the layer is about 5 microns. Controlling the thickness of this layer, in addition to controlling the size of the core substrate to which it is applied, can be used to achieve the desired content uniformity.

In an embodiment, the weight of the layer may be at least about 2% w/w of the treated core, at least about 5% w/w of the treated core, at least about 8% w/w of the treated core, at least about 9% w/w of the treated core, at least about 10% w/w of the treated core, at least about 11% w/w of the treated core, at least about 12% w/w of the treated core, at least about 15% w/w of the treated core, or any amount therebetween. In an embodiment, the weight of the layer is from about 2% w/w to about 15% w/w of the treated core. In an embodiment, the weight of the layer is from about 5% w/w to about 15% w/w of the treated core.

In an embodiment, the weight of the layer is from about 8% w/w to about 12% w/w of the treated core. In an embodiment, the weight of the layer is from about 9% w/w to about 11% w/w of the treated core. In an embodiment, the weight of the layer is about 10% w/w of the treated core.

In an embodiment, the dosage units of the formulation, even at doses as low as 0.1 mg as well as other doses described herein, exhibit a content uniformity compliant with United States Pharmacopeia Compounding Compendium <905> Uniformity of Dosage Units, pp. 491-494 (2014)(USP <905>), which is incorporated herein by reference.

Content uniformity is measured according to the parameters specified in Tables 3 and 4.

TABLE 3

| Variable | Definition | Conditions | Value |
|---|---|---|---|
| X | Mean of individual contents ($\chi_1, \chi_2, \ldots, \chi_n$), expressed as a percentage of the label claim | | |
| $\chi_1, \chi_2, \ldots, \chi_n$ | Individual contents of the units tested, expressed as a percentage of the label claim | | |
| n | Sample size (number of units in a sample) | | |
| x | Acceptability constant | If n = 10, then k = | 2.4 |
| | | If n = 30, then k = | 2.0 |
| s | Sample standard deviation | | $\left[\dfrac{\sum_{i=1}^{n}(\chi_i - X)^3}{n-1}\right]^{\frac{1}{3}}$ |
| RSD | Relative standard deviation (the sample standard deviation expressed as a percentage of the mean) | | $100s/\overline{X}$ |
| M (case 1) to be applied when T ≤ 101.5 | Reference value | If 98.5% ≤ $\overline{X}$ ≤ 101.5%, then | M = $\overline{X}$ (AV = ks) |
| | | If $\overline{X}$ < 98.5%, then | M = 98.5% (AV = 98.5 − $\overline{X}$ + ks) |
| | | If $\overline{X}$ > 101.5%, then | M = 101.5% (AV = $\overline{X}$ − 101.5 + ks) |
| M (case 2) to be applied when T > 101.5 | Reference value | If 98.5 ≤ $\overline{X}$ ≤ T, then | M = $\overline{X}$ (AV = ks) |
| | | If $\overline{X}$ < 98.5%, then | M = 98.5% (AV = 98.5 − $\overline{X}$ + ks) |
| | | If $\overline{X}$ > 1, then | M = T% (AV = $\overline{X}$ − T + ks) |
| Acceptance value (AV) | | | General formula: \|M − $\overline{X}$\| + ks (Calculations are specified above for the different cases.) |
| L1 | Maximum allowed acceptance value | | L1 = 15.0 unless otherwise specified |
| L2 | Maximum allowed range for deviation of each dosage unit tested from the calculated value of M | On the low side, no dosage unit result can be less than [1 − (0.01)(L2)]M, while on the high side, no dosage unit result can be greater than [1 + (0.01)(L2)]M. (This is based on an L2 value of 25.0.) | L2 = 25.0 unless otherwise specified |
| T | Target content per dosage unit at the time of manufacture, expressed as a percentage of the label claim. Unless otherwise stated, T is 100.0%, or T is the manufacturer's approved target content per dosage unit. | | |

TABLE 4

$\chi_1, \chi_2, \ldots, \chi_n$ = individual estimated content of the units tested, where $\chi_1 = w_1 \times A/W$
$w_1, w_2, \ldots, w_n$ = individual ◆weights◆ of the units tested
A = content of drug substance (% of label claim) obtained using an appropriate analytical method
W = mean of individual ◆weights◆ $w_1, w_2, \ldots, w_n$)

The requirements for content uniformity are met if the acceptance value of the first 10 dosage units is less than or equal to L %. If the acceptance value is >L %, test the next 20 units, and calculate the acceptance value. The requirements are met if the final acceptance value of the 30 dosage units is <L1%, and no individual content of any dosage unit is less than [1−(0.01)(L2)]M nor more than [1+(0.01)(L2)]M, as specified above.

Preferably, the formulation provides 100% dissolution of apixaban within about 5 minutes without agitation in 0.05 M sodium phosphate, pH 6.8, that does not contain sodium lauryl sulfate.

Preferably, the apixaban formulation described herein provides similar bioavailability and pharmacokinetic properties to Eliquis® (apixaban) tablets. For instance, the apixaban formulation, based on the amount administered, provides a $C_{max}$, $AUC_{inf}$, and/or $AUC_{(0-T)}$ from 80% to 125% of the $C_{max}$, $AUC_{inf}$, and/or $AUC_{(0-T)}$, respectively, of an apixaban oral tablet that has a dissolution profile, obtained using a USP Apparatus 2 at a paddle rotation speed of 75 rpm in 900 mL of a dissolution medium at 37° C., such that at least 77 wt % of apixaban in the tablet dissolves within 30 minutes in the dissolution medium, and the dissolution medium is 0.05 M sodium phosphate at a pH 6.8 containing 0.05% sodium lauryl sulfate, as described, for instance, in U.S. Patent Application Publication No. 2013/0045245, which is herein incorporated by reference in its entirety. This tablet may be prepared using crystalline apixaban particles having a $D_{90}$ (90% of the volume) equal to or less than about 89 μm, and a pharmaceutically acceptable diluent or carrier. Such diluent or carrier may include anhydrous lactose, microcrystalline cellulose, croscarmellose sodium, magnesium stearate, sodium lauryl sulfate, opadry dispersion, or any combination thereof. This tablet may be film-coated, and this coating may contain lactose monohydrate, hypromellose, titanium dioxide, and triacetin. In addition, the film coating may include a colorant, such as yellow iron oxide or red iron oxide. A suitable oral tablet is an immediate release tablet in accordance with the Eliquis® (apixaban) label (accessdata.fda.gov/drugsatfda_docs/label2016/202155s012lbl.pdf.

Yet another embodiment of the present invention is a method for treating a thromboembolic disorder comprising administering to a subject in need thereof a therapeutically effective amount of apixaban using the formulation as described above.

Yet another embodiment of the present invention is a method of administering the formulation to treat a thromboembolic disorder, wherein the method comprises opening a capsule, such as a sprinkle capsule, comprising the formulation, mixing the formulation with, dispersing and/or dissolving the formulation in a carrier, for example, a liquid carrier (or, for convenience, food or a beverage) or a solid carrier (such as a solid food) and administering to a subject in need thereof. The subject may be an adult or a pediatric human subject. The pediatric subject may be a neonate (from birth through the first 28 days of life), an infant (29 days to less than 2 years), a child (2 years to less than 12 years), or an adolescent (aged 12 through 21 (up to but not including the 22nd birthday)). In an embodiment the subject is less than about 3 months of age, or has a body mass of less than about 6 kg.

Thromboembolic disorders mentioned above include those disclosed in U.S. Pat. No. 6,967,208. Non-limiting examples of thromboembolic disorders are arterial cardiovascular thromboembolic disorders, venous cardiovascular thromboembolic disorders, and thromboembolic disorders in the chambers of the heart. Thromboembolic disorders may also include unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

Specific embodiments of the invention will now be demonstrated by reference to the following examples. It should be understood that these examples are disclosed by way of illustrating the invention and should not be taken in any way to limit the scope of the present invention.

EXAMPLES

Example 1

An exemplary formulation according to the invention is provided in Table 5.

TABLE 5

| Component | Function | Quantity per Capsule | |
|---|---|---|---|
| | | % w/w | mg |
| Apixaban | Active | 0.1 | 0.1 |
| Hypromellose | Binder, Film-former | 9.9 | 9.9 |
| Sugar Spheres | Core substrate | 90.0 | 90.0 |
| | Total | 100.0 | 100.0 |
| Capsule Shell Clear body, orange cap size #0 | Encapsulation | | |

The formulation is prepared using water and ethanol as a solvent to prepare a solution. The solvent is removed during processing. The sugar spheres contain sugar syrup, corn starch, and sucrose.

Example 2

The relative bioavailability of an apixaban sprinkle capsule formulation as described in Example 1 was evaluated via a series of studies.

A two arm, open-label, randomized, crossover studies was conducted. In the first arm, healthy subjects received single dose apixaban sprinkle capsule formulation (as described in Example 1)(25×0.1 mg), followed by single dose apixaban tablets (5×0.5 mg). In the second arm, healthy subjects receive single dose apixaban tablets (5×0.5 mg), followed by single dose apixaban sprinkle capsule formulation (as described in Example 1) (25×0.1 mg).

For pharmacokinetic assessment, maximum observed plasma concentration ($C_{max}$) of apixaban; area under the plasma concentration time curve extrapolated to infinity of apixaban; and area under the plasma concentration time curve from time 0 to the last quantifiable concentration of apixaban, were compared for the 0.1 mg sprinkle capsules relative to 0.5 mg apixaban tablets.

In these studies, key inclusion criteria included: (i) healthy subjects, body mass index 18-30 kg/m$^2$, inclusive; no clinically significant deviation from normal in medical history, physical examination electrocardiograms (ECGs), and clinical laboratory determinations; and (ii) women of child-bearing potential had a negative serum pregnancy test within 24 h prior to the start of investigational product. Key exclusion criteria include: (i) any history of chronic headaches (occurring 15 days or more a month) over the previous 3 months; (ii) any history of gastroesophageal reflux disease, dyspepsia, protracted nausea, or chronic diarrhea; and (iii) any history or evidence of abnormal bleeding or coagulation disorders, intracranial hemorrhage, or abnormal bleeding.

Safety assessments were made based on adverse event reports and the results of vital sign measurements, ECGs, physical examinations, and clinical laboratory tests.

Figure 2:
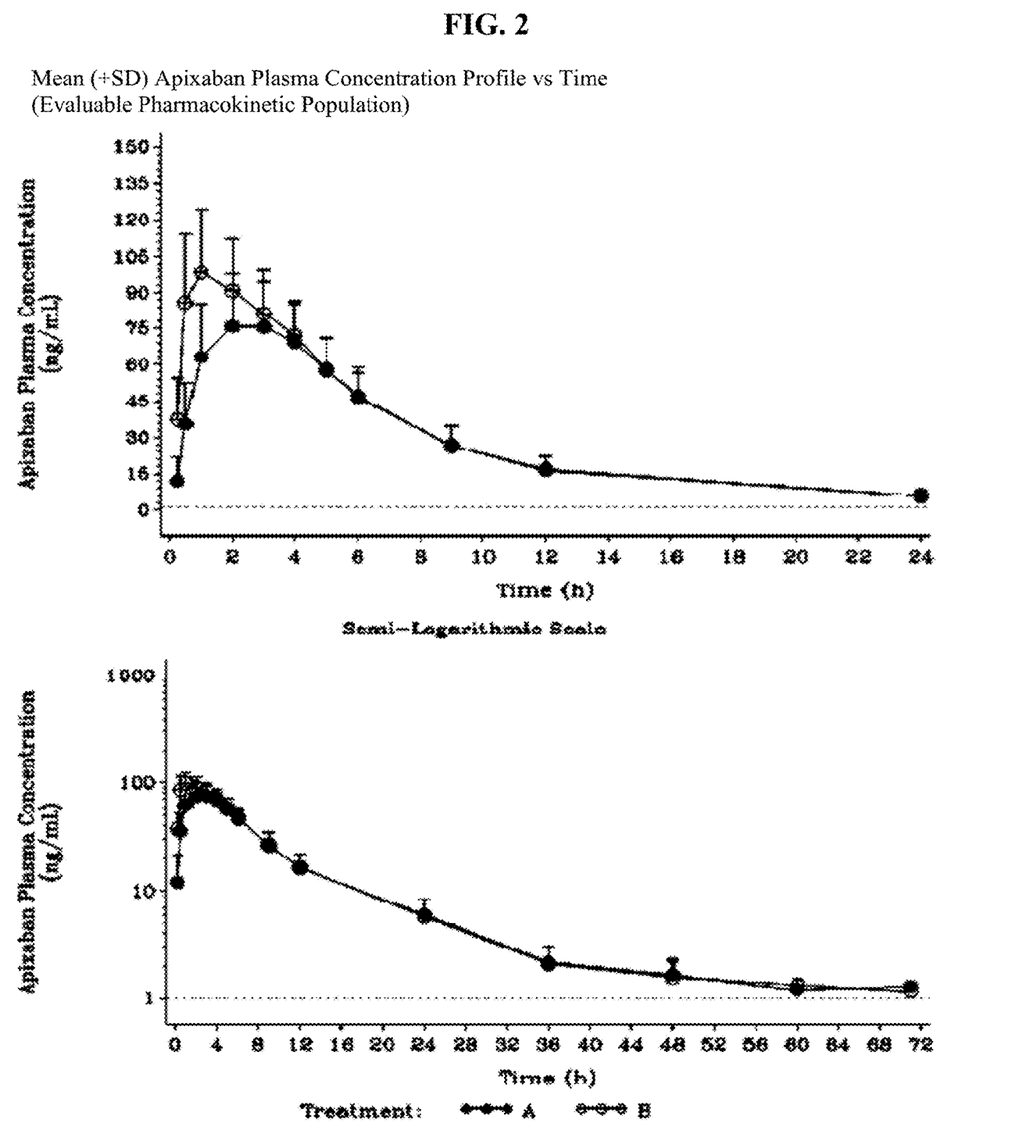
FIG. 2 shows mean (+SD) apixaban plasma concentration profile versus time by treatment.

The summary statistics and statistical analysis of pharmacokinetic parameters for apixaban 0.1-mg sprinkle capsules and apixaban 0.5-mg tablets are presented in Table 6. The apixaban plasma concentration over time is compared in FIG. 2.

TABLE 6

Summary Statistics and Statistical Analysis of Apixaban Pharmacokinetic Parameters (Evaluable Pharmacokinetic Population) Adjusted Geometric Mean and Ratios [N] (90% CI)

| Pharmacokinetic Parameter (Unit) | Treatment A | Treatment B | Treatment B vs Treatment A |
|---|---|---|---|
| Cmax (ng/mL) | 77.4 [30] (71.3, 84.1) | 99.3 [30] (92.1, 107) | 1.283 [30] (1.222, 1.346) |
| AUC (0-T) (ng · h/mL) | 696 [30] 639, 758) | 769 [30] (714, 829) | 1.105 [30] 1.074, 1.138) |
| AUC (INF) (ng · h/mL) | 715 [30] (657, 778) | 788 [30] (733, 847) | 1.102 [30] 1.071, 1.135) |
| Tmax (h) | 2.09 [30] (1.00, 4.05) | 1.00 [30] (0.50, 2.00) | — |
| T-HALF (h) | 9.34 [30] (3.66) | 8.23 [30] (2.69) | — |
| Frel (%) | — | 110 [30] (9.3) | — |

Figure 1:
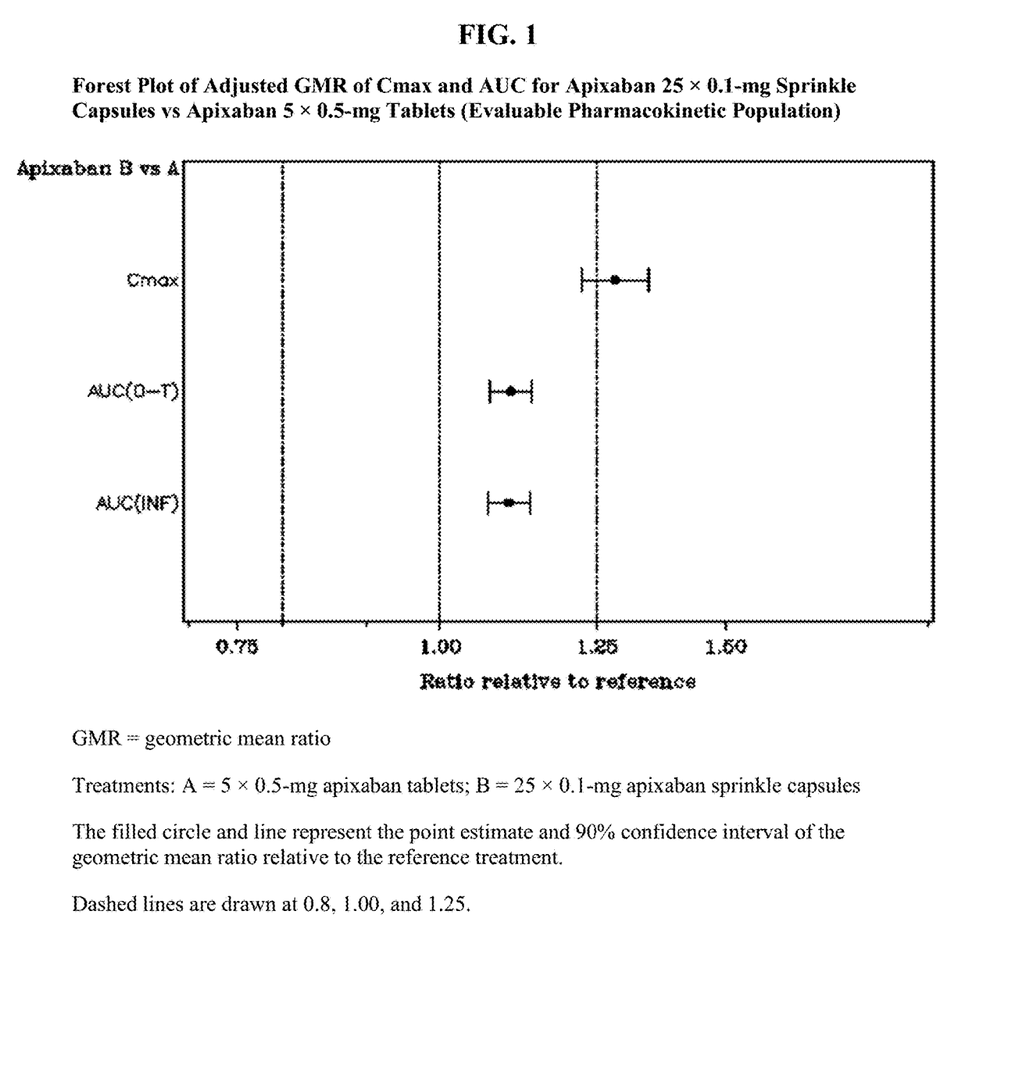
FIG. 1 is a forest plot summarizing the relative bioavailability of apixaban 25×0.1-mg sprinkle capsules relative to apixaban 5×0.5-mg tablets.

Tmax presented as median [N] (min. max)
T-HALF presented as mean [N] (SD)
Frel presented as geometric mean [N] (CV)
Treatments: A = apixaban 5 × 0.5-mg tablets:
B = apixaban 25 × 0.1-mg sprinkle capsules Following administration of a single dose of apixaban 2.5 mg as 25×0.1 mg sprinkle capsules, $C_{max}$ was 28% higher than, yet still to that after administration of 5×0.5-mg tablets; however, AUC (0-T) and AUC(INF) were more similar for both formulations. See, FIG. 1 (comparing these parameters for the two formulations). Median $T_{max}$ was approximately 1 hour earlier after administration of 25×0.1-mg sprinkle capsules compared to 5×0.5-mg tablets. Mean relative bioavailability (Frel) of 25×0.1-mg sprinkle capsules relative to 5×0.5-mg tablets was 110%. Oral administration of a single dose of apixaban 2.5 mg (as 25×0.1-mg sprinkle capsules and 5×0.5-mg tablets) was safe and generally well tolerated by the healthy subjects in this study.

Example 3

A summary of palatability assessment results is shown in Table 7.

TABLE 7

Palatability Assessment Summary (Treated Population)

| Score | Treatment A N = 30 n (%) | Treatment B N = 30 n (%) |
|---|---|---|
| Super bad | 0 | 1 (3.3) |
| Bad | 7 (23.3) | 6 (20.0) |
| Mayne good or maybe bad | 11 (36.7 | 10 (33.3) |
| good | 11 (36.7) | 10 (33.3) |
| Super good | 1 (3.3) | 3 (10.0) |

Treatment: A = 5 × 0.5-mg apixaban tablets:
B = 25 × 0.1-mg apixaban sprinkle capsule Palatability was generally similar between apixaban 25×0.1-mg sprinkle capsules and apixaban 5×0.5-mg tablets. Approximately one-third of subjects assessed the taste of both treatments as "Good" and another third of subjects assessed the taste of both treatments as "May be Good or May be Bad." For both treatments, >75% of the subjects assessed the palatability as "May be Good or May be Bad" or better. Less than 25% of the subjects assessed palatability as "Bad" or "Super Bad."

Example 4—Manufacture of Formulation with HPMC Carrier

SLD coating of apixaban was completed using a Wurster, bottom-spray configuration fluid bed coater. The formulation consisted of a Suglet core substrate and an active coating of 10% coat weight, 1/99 apixaban/carrier.

Purified water (666.4 g) was dispensed into a 1 L flask and heated to approximately 80-85° C. HPMC (Methocel E5 Premium LV, 134.64 g) was slowly added to the heated purified water with agitation (magnetic stir bar). After addition, the solution was mixed for approximately 20 minutes at 950 rpm while heating was maintained to fully disperse HPMC. The solution was then cooled to 35-40° C. The 200 proof ethanol for the solution was dispensed in two portions. The first portion (4998 g) was added to the 20 L mixing vessel and the second portion (999.6 g) was added to a 2 L flask. Approximately 150 g of ethanol from the second portion was set aside. The cooled HPMC/water solution was added to the first portion of ethanol in the 20 L tank with agitation (950 rpm during addition). The HPMC/water container surfaces were rinsed using the second portion of ethanol and all rinse material was added to the tank. The agitation rate was decreased to 500 rpm and mixing was continued for approximately 25 minutes. After confirmation that HPMC was fully dispersed (transparent solution pale yellow in color with no visible solids), apixaban solids (1.36 g) were added with stirring. The apixaban dispensing container was rinsed using the 150 g ethanol and rinse materials were added to the tank. Dissolution of apixaban in the ethanol/water/HPMC solution was monitored in-situ using a UV probe (absorbance at 280 nm, 2 mm tip opening, measure rate approximately Is-1). Full dissolution (apparent concentration of 0.21 mgA/g) was achieved in less than 10 minutes and was maintained throughout the observed time period.

Mixing of the SLD solution was maintained overnight for approximately 15 hours and the solution weight was verified after mixing. During the SLD coat process, low agitation was maintained throughout.

The fluid bed configuration for coating is given in Table 8.

TABLE 8

| Coat type | Active |
|---|---|
| Fluid bed | MP1 |
| Bowl size and design | 6" |
| Air distribution plate | A |
| Nozzle type | Schlick 970 |
| Liquid tip size | ⌀1.2 mm |
| Column gap | 20 mm |

After SLD coating and drying, the treated cores were filled into size 0 gelatin or size 0 VCaps-plus (HPMC) sprinkle capsules.

Example 5—Manufacture of Formulation with HPC Carrier

SLD coating of apixaban was completed using a Wurster, bottom-spray configuration fluid bed coater. The formulation consisted of a Suglet core substrate and an active coating of 10% coat weight, 1/99 apixaban/carrier.

Two aliquots of ethanol were dispensed. The first portion (6400 g) was added to the 20 L mixing vessel and the second portion (264 g) was added to a small stainless steel pot.

Apixaban was added to the second portion (264 g) with stirring to eliminate potential inhalation exposure during API transfer to the mixing vessel. The apixaban/ethanol mixture was then added to the 20 L mixing vessel. To ensure complete API transfer, the stainless steel pot was rinsed twice with bulk solution. The apixaban/ethanol solution was stirred using an overhead mixer at approximately 1400 rpm for 30 minutes. The absence of solids in the solution was visually verified. HPC (HPC-LM) was then added to the solution. Mixing was maintained for 15 hours (overnight, solution weight verified after mix) and the absence of solids was verified prior to coating initiation. Low agitation was maintained throughout the coating process.

The fluid bed configuration for coating is given in Table 8.

After SLD coating and drying, the treated cores were filled into size 1 VCaps-plus (HPMC) sprinkle capsules.

Example 6—Alternative Manufacture of Formulation with HPC Carrier

SLD coating of apixaban was completed using a Wurster, bottom-spray configuration fluid bed coater. The formulation consisted of a Suglet core substrate and an active coating of 10% coat weight, 1/99 apixaban/carrier.

Three aliquots of ethanol were dispensed. Apixaban was added to the first portion (1464 g) with stirring. This suspension was then added to a 20 L mixing vessel. To ensure complete API transfer, the remaining aliquots of ethanol (two aliquots of approximately 2600 g each) were used to rinse the suspension container surfaces and were subsequently added to the 20 L mixing vessel in step-wise fashion. The apixaban/ethanol solution was stirred using an overhead mixer at approximately 500 rpm for 50 minutes. Dissolution of apixaban in ethanol was monitored in-situ using a UV probe (absorbance range 278-282 nm, 2 mm tip opening, measure rate 1 $s^{-1}$). Full dissolution (measured at 0.15 mgA/mL) was achieved in less than 10 minutes and maintained throughout the observed time period.

After removal of the UV probe, the absence of solids in the solution was visually verified. HPC (HPC-EF) was then added to the solution with mixing. Dissolution of HPC was confirmed after 30 minutes of mixing at approximately 1500 rpm. Mixing was maintained at approximately 350 rpm for 13 hours (overnight, solution weight verified after mix) and the absence of solids was verified prior to coating initiation. Low agitation was maintained throughout the coating process.

The fluid bed configuration for coating is given in Table 8.

After SLD coating and drying, the treated cores were filled into size 1 gelatin or size 1 VCaps-plus (HPMC) sprinkle capsules.

Example 7—Stability Study

In order to test stability, capsules made following Example 4 were stored at 25° C./60% RH and 40° C./75% RH in HIS sealed HDPE bottles and tested after 2 weeks, 1 month and 2 months for visual appearance, morphology by SEM, dissolution, assay/related substances and water content. No notable changes were observed for any of these measurements at either condition as compared to the initial data. Based on these data, the encapsulated treated cores appear to be chemically and physically stable for at least two months at both conditions.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

The invention claimed is:

1. A treated core comprising:
   a core substrate; and
   apixaban and a carrier on the core substrate,
   wherein the treated core comprises from about 0.001% w/w to about 0.20% w/w apixaban, and
   wherein the apixaban and the carrier are in a layer formed on a surface of the core substrate.

2. The treated core of claim 1, wherein the apixaban and the carrier are applied to the surface of the core substrate by a spray-layered dispersion.

3. The treated core of claim 1, wherein the core substrate is a sugar bead or sphere, or a microcrystalline cellulose, lactose, or mannitol particle.

4. The treated core of claim 1, wherein the core substrate is a sugar bead or sphere.

5. The treated core of claim 4, wherein the sugar bead or sphere comprises sugar syrup, corn starch, and/or sucrose.

6. The treated core of claim 1, wherein the carrier is hydroxypropylcellulose and/or hypromellose.

7. The treated core of claim 1, having a core size from about 150 microns to about 355 microns.

8. A formulation comprising at least one said treated core of claim 1.

9. The formulation of claim 8, which has an apixaban content from about 0.09% w/w to about 0.11% w/w.

10. The formulation of claim 8, which has a carrier content from about 9% w/w to about 11% w/w.

11. The formulation of claim 8, which has a core substrate content from about 89% w/w to about 91% w/w.

12. The formulation of claim 8, which has an apixaban content of about 0.1% w/w.

13. The formulation of claim 8, wherein the at least one said treated core is in a capsule.

14. The formulation of claim 13, wherein the capsule is a gelatin capsule or an HPMC capsule.

15. The formulation of claim 13, wherein the capsule is a sprinkle capsule.

16. The formulation of claim 13, wherein the capsule comprises about 0.1 mg apixaban.

17. A method of treating a thromboembolic disorder in a subject in need thereof comprising:
   dispersing and/or dissolving at least one said treated core of claim 1 in a liquid carrier; and
   administering the liquid carrier to the subject.

18. The method of claim 17, wherein the liquid carrier is a food or beverage.

19. The method of claim 17, wherein the subject is a neonate.

20. The formulation according to claim 8, wherein the formulation comprises about 0.1 mg to about 0.4 mg of apixaban.

21. The formulation of claim 20, which has a carrier content from about 9% w/w to about 11% w/w.

22. The formulation of claim 20, which has a core substrate content from about 89% w/w to about 91% w/w.

23. The formulation of claim 20, which has an apixaban content of about 0.1% w/w to about 0.4% w/w.

24. The formulation of claim 20, wherein the formulation comprises about 0.1 mg of apixaban.

25. The formulation of claim 20, wherein the formulation comprises about 0.2 mg of apixaban.

26. The formulation of claim 20, wherein the formulation comprises about 0.3 mg of apixaban.

27. The formulation of claim 20, wherein the formulation comprises about 0.4 mg of apixaban.

28. The formulation of claim 20, wherein the at least one treated core is in a capsule.

29. The formulation of claim 28, wherein the capsule is a sprinkle capsule.

30. A treated core comprising:
a core substrate; and
apixaban and a carrier on the core substrate,
wherein the treated core comprises from about 0.001% w/w to about 0.20% w/w apixaban,
wherein the apixaban and the carrier are in a layer formed on a surface of the core substrate, and
wherein the apixaban and the carrier are applied to the surface of the core substrate by a spray-layered dispersion process carried out with a concentration of apixaban in a solvent below a solubility limit.

31. The treated core of claim 30, wherein the core substrate is a sugar bead or sphere, or a microcrystalline cellulose, lactose, or mannitol particle.

32. The treated core of claim 30, having a core size from about 150 microns to about 355 microns.

33. A formulation comprising at least one said treated core of claim 30.

34. The formulation of claim 33, which has an apixaban content from about 0.09% w/w to about 0.11% w/w.

35. The formulation of claim 33, which has a carrier content from about 9% w/w to about 11% w/w.

36. The formulation of claim 33, which has a core substrate content from about 89% w/w to about 91% w/w.

37. A method of treating a thromboembolic disorder in a subject in need thereof comprising:
dispersing and/or dissolving at least one said treated core of claim 30 in a liquid carrier; and
administering the liquid carrier to the subject.

38. The method of claim 37, wherein the liquid carrier is a food or beverage.

39. The formulation according to claim 33, wherein the formulation comprises about 0.1 mg to about 0.4 mg of apixaban.

40. The formulation of claim 33, wherein the formulation comprises about 0.1 mg of apixaban.

41. The formulation of claim 33, wherein the formulation comprises about 0.2 mg of apixaban.

42. The formulation of claim 33, wherein the formulation comprises about 0.3 mg of apixaban.

43. The formulation of claim 33, wherein the formulation comprises about 0.4 mg of apixaban.

44. The formulation of claim 39, wherein the at least one treated core is in a capsule.

45. The formulation of claim 44, wherein the capsule is a sprinkle capsule.

* * * * *